United States Patent [19]

Fuchs et al.

[11] 4,218,469
[45] Aug. 19, 1980

[54] COMBATING ARTHROPODS WITH 3-PHENOXY-FLUORO-BENZYL CARBOXYLIC ACID ESTERS

[75] Inventors: Rainer Fuchs, Wuppertal; Ingeborg Hammann, Cologne; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 877,536

[22] Filed: Feb. 13, 1978

[30] Foreign Application Priority Data

Mar. 3, 1977 [DE]  Fed. Rep. of Germany ....... 2709264

[51] Int. Cl.$^2$ .......... A01N 9/20; A01N 9/24; C07C 69/74; C07C 121/75
[52] U.S. Cl. .............. 424/304; 260/340.5 R; 260/465 D; 260/465 F; 424/282; 424/305; 424/306; 424/308; 424/309; 560/9; 560/20; 560/55; 560/105; 560/124; 568/637; 568/639
[58] Field of Search .............. 260/465 D, 340.5 R; 560/124, 105, 9, 20, 55; 424/304, 305, 308, 282

[56]  References Cited
U.S. PATENT DOCUMENTS

| 3,666,789 | 5/1972 | Itaya et al. ............. 424/305 X |
| 3,835,176 | 9/1974 | Matsuo et al. ............. 260/465 D |
| 3,973,036 | 8/1976 | Hirano et al. ............. 424/304 |
| 3,996,244 | 12/1976 | Fujimoto et al. ............. 424/304 X |

*Primary Examiner*—Dolph H. Torrence
*Attorney, Agent, or Firm*—Sprung, Felfe, Horn, Lynch & Kramer

[57]  ABSTRACT

3-Phenoxy-fluoro-benzyl carboxylic acid esters of the formula

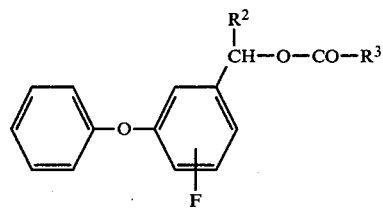

(I)

in which
R$^2$ is hydrogen, cyano or ethynyl,
R$^3$ is

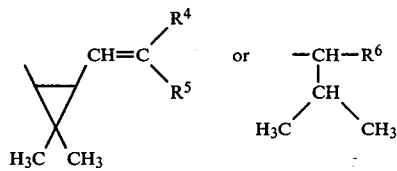

R$^4$ and R$^5$ represent chlorine, bromine or methyl, and
R$^6$ is phenyl or phenyl substituted with halogen, alkyl with 1 to 4 carbon atoms, alkoxy with 1 to 4 carbon atoms, nitro or methylenedioxy, which possess arthropodicidal properties. The alcohols are also new.

10 Claims, No Drawings

COMBATING ARTHROPODS WITH 3-PHENOXY-FLUORO-BENZYL CARBOXYLIC ACID ESTERS

The present invention relates to and has for its objects the provision of particular new 3-phenoxy-fluoro-benzyl carboxylic acid esters which possess arthropodicidal properties, active compositions in the form of mixtures of such compounds with solids and liquid dispersible carrier vehicles, and methods for producing such compounds and for using such compounds in a new way especially for combating pests, e.g. arthropods, with other and further objects becoming apparent from a study of the within specification and accompanying examples.

It is already known the phenoxybenzyl acetates or carboxylates, such as, for example, 3'-phenoxybenzyl α-isopropyl-(3,4-dimethoxyphenyl)-acetate and 3'-[2-fluoro- or 4-fluoro-phenoxy]-α-cyanobenzyl [2,2-dimethyl-3-(2,2-dichlorovinyl)-cyclopropane]-carboxylate, possess insecticidal and acaricidal properties (U.S. Pat. Nos. 3,996,244 and 4,016,179 and Belgian Patent Specification 801,946).

The present invention now provides, as new compounds, the substituted phenoxybenzyloxycarbonyl derivatives of the general formula

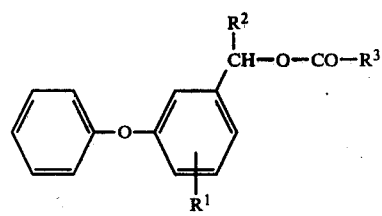

(I)

in which
  $R^1$ represents fluorine,
  $R^2$ represents hydrogen, cyano or ethynyl,
  $R^3$ represents the radical

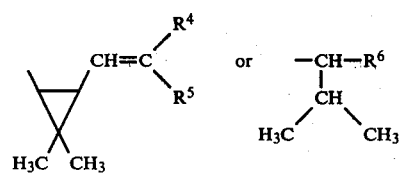

wherein
  $R^4$ and $R^5$ are identical and represent chlorine, bromine or methyl, and
  $R^6$ represents a phenyl ring which optionally carries one or more substituents selected independently from halogen, alkyl with 1 to 4 carbon atoms, alkylthio with 1 to 4 carbon atoms, alkoxy with 1 to 4 carbon atoms, nitro and methylenedioxy.

Preferably, $R^1$ represents fluorine, $R^2$ represents hydrogen or cyano and $R^3$ represents a 2,2-dimethyl-3-(2,2-dichlorovinyl)-cyclopropane, 2,2-dimethyl-3-(2,2-dibromovinyl)-cyclopropane or 2,2-dimethyl-3-(2,2-dimethylvinyl)-cyclopropane radical or represents an α-isopropylbenzyl radical, the ring of which can optionally carry one or more substituents selected independently from fluorine, chlorine, bromine, methylenedioxy, methoxy, ethoxy, methylthio, ethylthio, straight-chain or branched alkyl with 1 to 3 carbon atoms and nitro.

The general formula (I) includes here the various possible stereoisomers, the optical isomers and mixtures of these components.

Surprisingly, the substituted phenoxybenzyloxycarbonyl derivatives according to the invention exhibit a better insecticidal and acaricidal action than the corresponding previously known products of analogous structure and the same type of action. The products according to the present invention thus represent a true enrichment of the art.

The invention also provides a process for the preparation of a substituted phenoxybenzyloxycarbonyl derivative of the formula (I), in which a carbonyl halide of the general formula

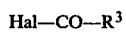 Hal—CO—$R^3$  (II), in which
  $R^3$ has the meaning stated above and
  Hal represents halogen, preferably chlorine, is reacted with a substituted phenoxybenzyl alcohol of the general formula

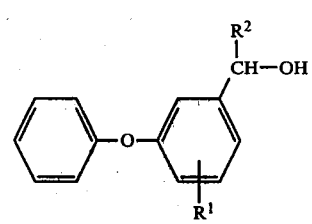

(III), in which
  $R^1$ and $R^2$ have the meanings stated above, optionally in the presence of an acid acceptor and optionally in the presence of a solvent or diluent. If, for example, 2-fluoro-5-phenoxy-α-cyanobenzyl alcohol and α-isopropyl-4-ethoxyphenylacetyl chloride are used as the starting materials, the course of the reaction can be represented by the following equation:

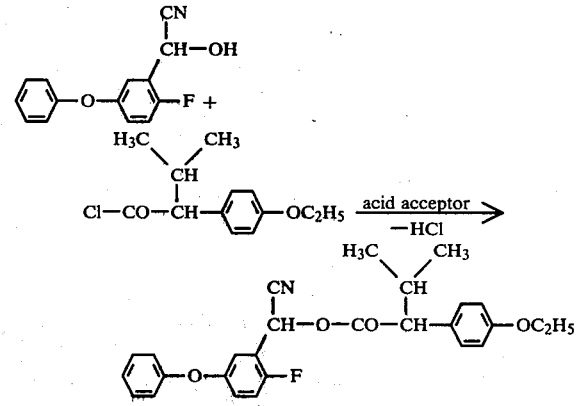

The carbonyl halides of the general formula (II) to be used as starting materials are known and can be prepared by processes which are generally customary and are described in the literature (see, for example, German Offenlegungsschriften (German Published Specifications) 2,365,555; 1,926,433 and 2,231,312).

Examples of the compounds (II) which may be mentioned are: 2,2-dimethyl-3-(2,2-dichlorovinyl)-cyclopropanecarboxylic acid chloride, 2,2-dimethyl-3-(2,2-dibromovinyl)-cyclopropanecarboxylic acid chloride, 2,2-dimethyl-3-(2,2-dimethylvinyl)-cyclopropanecarboxylic acid chloride, α-isopropyl-phenylacetyl chloride, α-isopropyl-4-fluorophenylacetyl chloride, α-isopropyl-4-chlorophenylacetyl chloride, α-isopropyl-4-bromophenylacetyl chloride, α-isopropyl-4-methylphenylacetyl chloride, α-isopropyl-4-ethylphenylacetyl chloride, α-isopropyl-4-n-propyl-phenylacetyl chloride, α-isopropyl-4-iso-propylphenylacetyl chloride, α-isopropyl-4-methoxyphenylacetyl chloride, α-isopropyl-4-ethoxy-phenylacetyl chloride, α-isopropyl-4-methylthiophenylacetyl chloride, α-isopropyl-4-ethylthiophenylacetyl chloride, α-isopropyl-4-nitrophenylacetyl chloride, α-isopropyl-3-fluorophenylacetyl chloride, α-isopropyl-3-bromophenylacetyl chloride, α-isopropyl-3-chlorophenylacetyl chloride, α-isopropyl-3-methylphenylacetyl chloride, α-isopropyl-3-ethylphenylacetyl chloride, α-isopropyl-3-methoxyphenylacetyl chloride, α-isopropyl-3-ethoxyphenylacetyl chloride, α-isopropyl-3-methylthiophenylacetyl chloride, α-isopropyl-3-ethylthiophenylacetyl chloride and α-isopropyl-3,4-methylene-dioxyphenylacetyl chloride.

The phenoxybenzyl alcohols of the general formula (III) which are also to be used as starting compounds have not hitherto been described in the literature. They are obtained by a process in which phenoxybenzaldehydes of the general formula

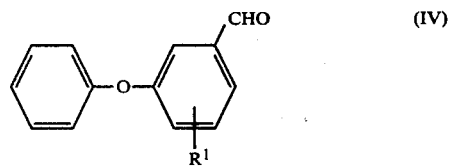

in which
R¹ has the meaning stated above,
(a), in the case where R² represents hydrogen, are reduced with a complex metal hydride in an inert solvent,
(b), in the case where R² represents cyano, are reacted with an alkali metal cyanide, for example sodium cyanide or potassium cyanide, in the presence of an acid, optionally with the addition of a solvent, or
(c), in the case where R² represents ethynyl, are reacted with an ethynyl compound of the formula HC≡C—MgHal¹ (V), in which
Hal¹ represents halogen, especially bromine, in a suitable solvent.

If, for example, 5-phenoxy-2-fluoro-benzaldehyde and lithium aluminum hydride are used as starting materials according to process variant (a), 5-phenoxy-2-fluorobenzaldehyde and potassium cyanide are used as starting materials according to process variant (b) and 5-phenoxy-2-fluorobenzaldehyde and ethynylmagnesium bromide are used as starting materials according to process variant (c), the course of the reactions can be represented by the following equations:

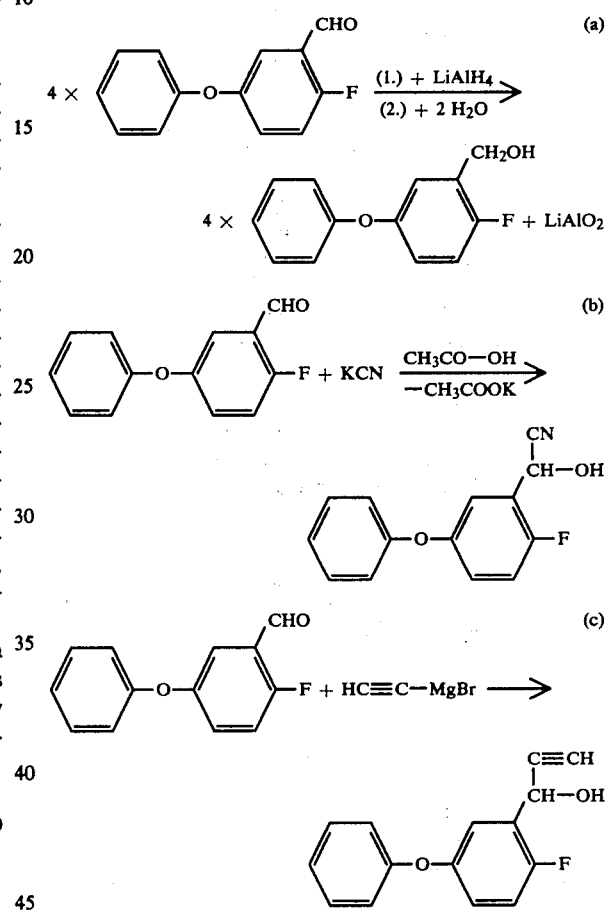

The ethynyl compounds of the formula (V) are described in the literature, as are the alkali metal cyanides and complex metal hydrides.

The phenoxy-benzaldehydes of the formula (IV) can be prepared by generally customary processes, and in particular, for example, by reacting the corresponding phenoxybenzyl halides of the general formula (IV) below, which are prepared from the corresponding phenoxytoluenes by customary methods, with hexamethylenetetramine according to the following scheme:

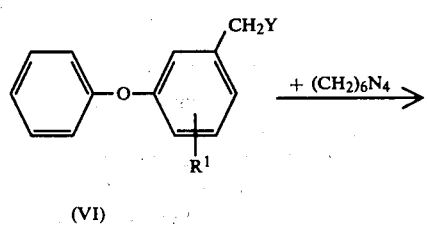

(VI)

-continued

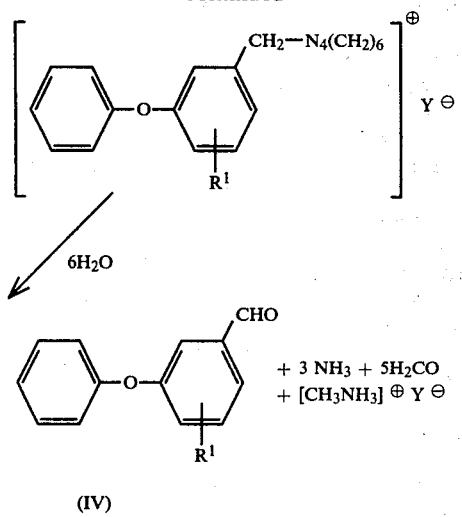

(IV)

wherein
R¹ has the meaning stated above and
Y represents halogen.

Examples which may be mentioned of the phenoxybenzaldehydes to be reacted according to the process are: 3-phenoxy-4-fluoro-benzaldehyde, 5-phenoxy-2-fluoro-benzaldehyde and 3-fluoro-5-phenoxy-benzaldehyde.

Variants (a) to (c) for the preparation of the phenoxybenzyl alcohols of the general formula (III) are preferably carried out using suitable solvents or diluents at the same time.

Preferred solvents or diluents for carrying out process variant (a) are ethers, such as diethyl ether, tetrahydrofuran and dioxane as well as hydrocarbons, such as toluene and benzine. When sodium borohydride is used as the reducing agent, water, alcohols, such as methanol or ethanol, or nitriles, such as acetonitrile or propionitrile, can additionally be used. Preferred solvents or diluents for carrying out process variant (b) are water, alcohols, such as methanol or ethanol, ethers, such as diethyl ether or tetrahydrofuran, or nitriles, such as acetonitrile. Preferred solvents or diluents for process variant (c) are ethers, such as diethyl ether, tetrahydrofuran and dioxane.

Complex metal hydrides which may be mentioned as preferred for process variant (a) are lithium aluminum hydride and sodium borohydride.

Acids which can be used in process variant (b) are inorganic acids, for example hydrochloric acid or sulphuric acid, or organic acids, for example acetic acid or formic acid.

In all process variants, the reaction temperature can be varied within a relatively wide range. In general, the reaction is carried out at from −10° to 110° C.; in variant (a) it is preferably carried out at 0° to 60° C., in variant (b) it is preferably carried out at from −5° to 20° C. and in variant (c) it is preferably carried out at from 0° to 80° C.

In general, the reactions are allowed to proceed under normal pressure.

In carrying out variant (a), the reactants are preferably employed in equimolar amounts. An excess of one or other component provides no advantage. In variant (b) the cyanide is preferably employed in 100–150% excess. The reaction is preferably carried out in one of the solvents or diluents indicated above at the temperatures indicated, whilst stirring. After a reaction time of one or more hours, usually at elevated temperature, the reaction mixture is worked up by methods which are generally customary.

The new compounds (III) are obtained in the form of oils, which either can be distilled or are freed from the last volatile constituents by so-called "incipient distillation", that is to say by prolonged heating to moderately elevated temperatures under reduced pressure, and are purified in this manner. The refractive index or the boiling point is used for their characterization.

Examples which may be mentioned of the new phenoxybenzyl alcohols of the general formula (III) which can be used for the preparation of the phenoxybenzyloxycarbonyl derivatives of the general formula (I) are: 3-phenoxy-4-fluorobenzyl alcohol, 5-phenoxy-2-fluoro-benzyl alcohol, 3-fluoro-5-phenoxy-benzyl alcohol, 3-phenoxy-4-fluoro-α-cyanobenzyl alcohol, 5-phenoxy-2-fluoro-α-cyanobenzyl alcohol, 3-fluoro-5-phenoxy-α-cyanobenzyl alcohol, 3-phenoxy-4-fluoro-α-ethynyl-benzyl alcohol, 5-phenoxy-2-fluoro-α-ethynylbenzyl alcohol and 3-fluoro-5-phenoxy-α-ethynylbenzyl alcohol.

All the customary acid-binding agents can be used as acid acceptors in the preparation of the phenoxybenzyloxycarbonyl derivatives according to the invention. Alkali metal carbonates and alcoholates, such as sodium carbonate and potassium carbonate, sodium methylate and ethylate and potassium methylate and ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a relatively wide range. In general, the reaction is carried out at from 0° to 100° C., preferably at from 15° to 40° C.

In general, the reaction is allowed to proceed under normal pressure.

The process for the preparation of the compounds of the formula (I) according to the invention is preferably carried out using a suitable solvent or diluent. Possible solvents are virtually all the inert organic solvents, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane ketones, for example acetone, methyl ethyl ketone, methyl isopropyl ketone and methyl isobutyl ketone; and nitriles, such as acetonitrile and propionitrile.

In carrying out the process, the starting materials are preferably employed in equimolar amounts. An excess of one or other reactant provides no substantial advantages. In general, the reactants are brought together in one of the solvents indicated and the mixture is stirred for one or more hours, usually at elevated temperature, in order to bring the reaction to completion. The reaction mixture is then poured into water and the organic phase is separated off and rinsed with water. After drying, the solvent is distilled off in vacuo.

The compounds of the formula (I) are obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. The refractive index is used for their characterization.

As already mentioned, the substituted phenoxybenzyloxy-carbonyl derivatives according to the invention are distinguished by an outstanding insecticidal and acaricidal activity.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development.

The abovementioned pests include:

from the class of the Isopoda, for example *Oniscus asellus, Armadillidium vulgare* and *Porcellio scaber*;

from the class of the Diplopoda, for example *Blaniulus guttulatus*;

from the class of the Chilopoda, for example *Geophilus carpophagus* and Scutigera spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis, Periplanta americana, Leucophaea maderae, Blattella germanica, Acheta domesticus,* Gryllotalpa spp., *Locusta migratoria migratorioides, Melanoplus differentialis* and *Schistocerca gregaria*;

from the order of the Dermaptera, for example *Forficula auricularia*;

from the order of the Isoptera, for example Reticulitermes spp.;

from the order of the Anoplura, for example *Phylloxera vastatrix*, Pemphigus spp., *Pediculus humanus, corporis,* Haematopinus spp. and Linognathus spp., from the order of the Mallophaga, for example Trichodectes spp. and Damalinea spp.;

from the order of the Thysanoptera, for example *Hercinothrips fermoralis* and *Thrips tabaci*;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistics citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., Psylliodes chrysocephala, *Epilachna varivestis,* Atomaria spp., Oryzaephilus *surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*;

from the order of the Siphonaptera, for example *Xenopsylla cheopis* and Ceratophyllus spp.;

from the class of the Arachnida, for example *Scorpio maurus* and *Latrodectus mactans*;

from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The compounds according to the invention exhibit powerful ectoparasiticidal and tickicidal properties, especially against ticks which, as animal ectoparasites, attack domesticated animals, such as, for example, cattle and sheep. However, as mentioned above, the active compounds according to the invention have a favorable level of toxicity towards warm-blooded animals. They are therefore very suitable for combating animal ectoparasites, especially ticks.

As economically important ectoparasites of this type, which play a major role especially in tropical and subtropical countries, there may be mentioned, for example, the Australian and South American single-host cattle tick *Boophilus microplus,* the South African cattle tick *Boophilus decoloratus,* both from the family of the Ixodidae, the African multi-host cattle ticks and sheep ticks, such as, for example, *Rhipicephalus appendiculatus, Rhipicephalus evertsi, Amblyomma hebraeum* and *Hyalomma Aruncatum* and the South American multi-host cattle ticks such as, for example, *Amblyomma cajennense* and *Amblyomma americanum.*

In the course of time such ticks have, in numerous areas, become resistant to the phosphoric acid esters and carbamates hitherto used as combating agents, so that the success of combating them has in many areas become increasingly dubious. To ensure economical stock raising in the infected areas, there is an urgent need for agents by means of which all stages of deveopment, that is to say larvae, metalarvae, nymphs, metanymphs and adults, even of resistant strains, for example of the genus Boophilus, can be combated reliably. For example, in Australia the Mackay strain, the Mount Alfort strain and the Biarra strain of *Boophilus microplus* are highly resistant to the phosphoric acid ester agents used hitherto.

The active compounds according to the invention are equally effective against both the normally sensitive strains and the resistant strains, for example of Boophilus. When applied in the usual manner to the host animal, they have a direct destructive effect on all forms parasitic on the animal, so that the development cycle of the ticks is interrupted in the parasitic phase on the animal.

The laying of fertile eggs and hence the development and slipping of the larvae is inhibited.

The compounds are used, for example, in a dip or bath, in which case the active compounds in the dirtied aqueous dip liquor, which is exposed to microbial attack, must remain stable for 6 months or longer. Other methods of application include spraying and pouring.

In all use forms, the compounds according to the invention are completely stable, that is to say no decrease in action is detectable after 6 months.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, bactericides, rodenticides, herbicides, fertilizers growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e, an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

The phenoxybenzyl alcohols required as starting compounds can be prepared, for example, as follows:

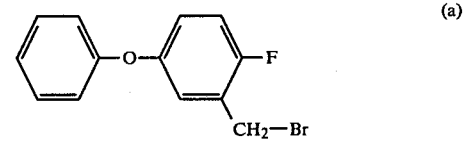

(a)

90 g (0.445 mol) of 2-fluoro-5-phenoxy-toluene were dissolved in 300 ml of anhydrous carbon tetrachloride and the solution was heated under reflux, together with 79.3 g of N-bromosuccinimide. After a temperature of 70° C. had been reached, 5 g of azodiisobutyronitrile were added and after about 10–20 minutes, the reaction began, with the evolution of heat. After the exothermic reaction had subsided, the mixture was heated under reflux for a further 4 hours. The reaction mixture was then cooled to 10° C., the succinimide was filtered off and the carbon tetrachloride was distilled off in vacuo. The oil which remained was distilled at 142°–148° C./2 mm Hg. This gave 2-fluoro-5-phenoxy-benzyl bromide in a yield of 56%.

The compounds of the formula

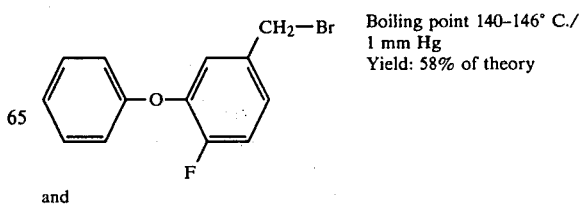

Boiling point 140–146° C./ 1 mm Hg
Yield: 58% of theory and

-continued

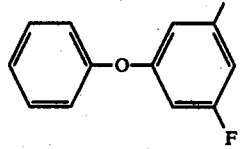
Boiling point 145–150° C./4 mm Hg
Yield: 61% of theory could be prepared analogously.

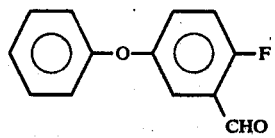

(b)

48 g (0.17 mol) of 2-fluoro-5-phenoxy-benzyl bromide and 47.8 g of hexamethylenetetramine in 250 ml of methylene chloride were heated under reflux for 3 hours, the mixture was then cooled to 5°–10° C. and the precipitate which had formed was filtered off. This precipitate was washed with 100 ml of methylene chloride, sucked dry and then heated under reflux for 5 hours in 100 ml of 50% strength aqueous acetic acid. Thereafter, 25 ml of concentrated hydrochloric acid were added and the mixture was again heated under reflux for 30 minutes and then cooled to 10°–20° C. 200 ml of water were added to the reaction mixture and this was extracted twice with 150 ml of ether each time and the combined ether phases were then washed with sodium bicarbonate solution and dried over sodium sulphate. The ether was distilled off in vacuo. This gave 2-fluoro-5-phenoxy-benzaldehyde with a boiling point of 130°–138° C./1 mm Hg in a yield of 42%.

The compound of the formula

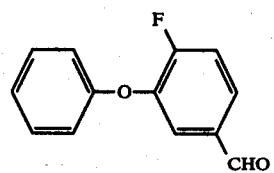
Boiling point 132–135° C./2 mm Hg
Yield: 62% of theory could be prepared analogously.

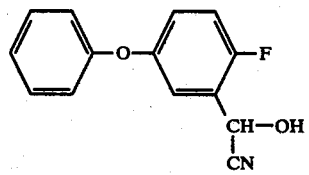

(c₁)

21.6 g (0.1 mol) of 2-fluoro-5-phenoxy-benzaldehyde were dissolved in 25 ml of glacial acetic acid and 10.2 g of sodium cyanide dissolved in 25 ml of water were added dropwise at 15° C., while stirring. The reaction mixture was then stirred for 8 hours at 20° C., poured into 100 ml of water and extracted with 200 ml of ether and the ether phase was separated off. In order to remove the glacial acetic acid, the ether phase was washed with dilute sodium bicarbonate solution and then dried over sodium sulphate. After distilling off the ether in vacuo, 2-fluoro-5-phenoxy-α-cyanobenzyl alcohol having a refractive index $n_D^{23}$ of 1.5657 was obtained in a yield of 85%.

The compound of the formula

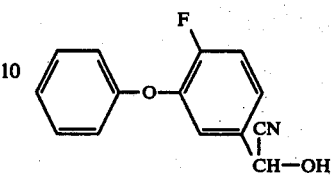
Refractive index: $n_D^{21}$: 1.5589
Yield: 87% of theory could be prepared analogously.

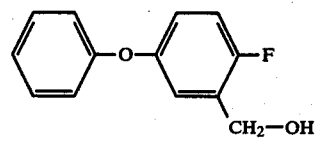

(c₂)

54 g (0.25 mol) of 2-fluoro-5-phenoxy-benzaldehyde dissolved in 50 ml of dry ether were added dropwise, at the boil, to 3.8 g of lithium aluminum hydride in 100 ml of anhydrous ether, while stirring well. The reaction mixture was subsequently stirred for a further 10 hours at 22° C. and then cooled to 0° C., and ice-water was added dropwise, while stirring, until no further evolution of hydrogen could be observed. The precipitate which had formed was dissolved by adding 10% sulphuric acid and the reaction mixture was then extracted twice with 100 ml of ether each time. The ether phases were separated off, washed with saturated sodium chloride solution and dried over sodium sulphate.

After distilling off the ether in vacuo, 2-fluoro-5-phenoxybenzyl alcohol with a boiling point of 161°–165° C./4 mm Hg was obtained in a yield of 90%.

The compound of the formula

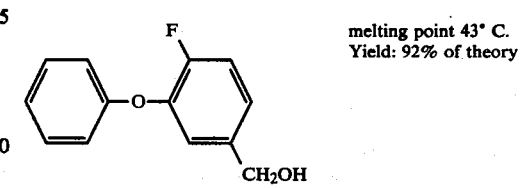
melting point 43° C.
Yield: 92% of theory could be prepared analogously.

EXAMPLE 2

The end products were prepared as follows:

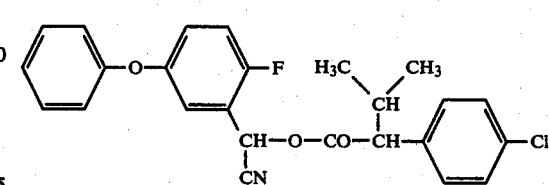

(1)

8 g (0.033 mol) of 2-fluoro-5-phenoxy-α-cyanobenzyl alcohol and 7.6 g (0.033 mol) of α-isopropyl-4-chlorophenylacetyl chloride were dissolved in 150 ml of anhydrous toluene and 2.64 g (0.033 mol) of pyridine dissolved in 50 ml of toluene were added dropwise at 25°-30° C., whilst stirring. The mixture was then stirred for a further 3 hours at 25° C. The reaction mixture was poured into 150 ml of water and the organic phase was separated off and washed again with 100 ml of water. The toluene phase was then dried over sodium sulphate and the solvent was distilled off under a water pump vacuum. The last residues of solvent were removed by brief incipient distillation at a bath temperature of 60° C. and under a pressure of 1 mm Hg. This gave 11.0 g (76.2% of theory) of 2'-fluoro-5'-phenoxy-α'-cyanobenzyl α-isopropyl-4-chlorophenyl acetate as a yellow oil having a refractive index $n_D^{26}$ of 1.5473.

EXAMPLE 3

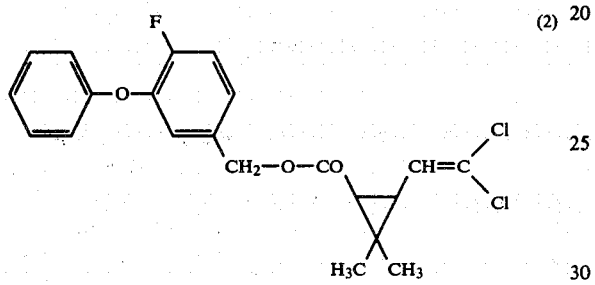

(2)

2.18 g (0.01 mol) of 3-phenoxy-4-fluoro-benzyl alcohol and 2.28 g (0.01 mol) of 2,2-dimethyl-3-(2,2-dichlorovinyl)cyclopropanecarboxylic acid chloride were dissolved in 100 ml of anhydrous toluene, and 0.8 g (0.01 mol) of pyridine dissolved in 50 ml of toluene was added dropwise at 25°-30° C., while stirring. The mixture was then stirred for a further 3 hours at 25° C. The reaction mixture was then poured into 150 ml of water and the toluene phase was separated off and washed again with 100 ml of water. The organic phase was dried over sodium sulphate and the toluene was then distilled off under a water pump vacuum. The last residues of solvent were removed by incipient distillation at a bath temperature of 60° C. and under a pressure of 1 mm Hg. This gave 3.5 g (85.6% of theory) of 3'-phenoxy-4'-fluoro-benzyl 2,2-dimethyl-3-(2,2-dichlorovinyl)-cyclopropane-carboxylate as a yellow oil having a refractive index $n_D^{23}$ of 1.5548.

The following compounds of the formula

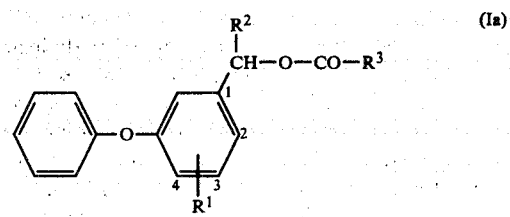

(Ia)

could be prepared analogously:

TABLE 1

| Compound No. | $R^1$ | $R^2$ | $R^3$ | Refractive index | Yield (% of theory) |
|---|---|---|---|---|---|
| 3 | 2-F | CN | ![structure: CH=CCl2 with cyclopropane bearing H3C, CH3] | $n_D^{26}$:1.5435 | 71 |
| 4 | 2-F | H | ![structure: CH=CCl2 with cyclopropane bearing H3C, CH3] | $n_D^{25}$:1.5555 | 68 |
| 5 | 4-F | H | ![structure: -CH-CH(iPr)-C6H4-Cl] | $n_D^{25}$:1.5601 | 72 |
| 6 | 4-F | CN | ![structure: CH=CCl2 with cyclopropane bearing H3C, CH3] | $n_D^{23}$:1.5511 | 82 |

TABLE 1-continued

| Compound No. | R¹ | R² | R³ | Refractive index | Yield (% of theory) |
|---|---|---|---|---|---|
| 7 | 4-F | CN | —CH(CH(CH₃)₂)—C₆H₄—4-Cl | $n_D^{23}$:1.5581 | |
| 8 | 4-F | CN | 2,2-dimethylcyclopropyl—CH=C(Br)₂ | $n_D^{25}$:1.5684 | 82 |
| 9 | 4-F | H | 2,2-dimethylcyclopropyl—CH=C(Br)₂ | $n_D^{25}$:1.5723 | |
| 10 | 4-F | CN | 2,2-dimethylcyclopropyl—CH=C(Br)₂ | $n_D^{25}$:1.5684 | 76 |
| 11 | 4-F | CN | 2,2-dimethylcyclopropyl—CH=C(CH₃)₂ | $n_D^{25}$:1.5381 | 82 |
| 12 | 4-F | C≡CH | 2,2-dimethylcyclopropyl—CH=C(Cl)₂ | | |
| 13 | 2-F | CN | —CH(CH(CH₃)₂)—C₆H₄—4-Br | | |
| 14 | 2-F | H | 2,2-dimethylcyclopropyl—CH=C(Br)₂ | | |
| 15 | 4-F | H | 2,2-dimethylcyclopropyl—CH=C(CH₃)₂ | | |

TABLE 1-continued
| Compound No. | R¹ | R² | R³ | Refractive index | Yield (% of theory) |
|---|---|---|---|---|---|
| 16 | 2-F | C≡CH | 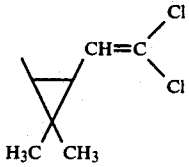 | | |
| 17 | 4-F | C≡CH | 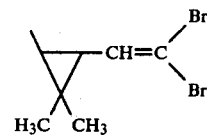 | | |
| 18 | 2-F | CN | 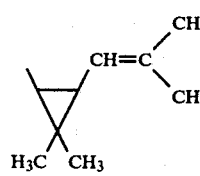 | | |
| 19 | 4-F | CN | 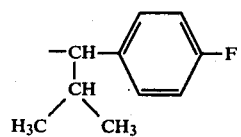 | | |
| 20 | 4-F | CN | 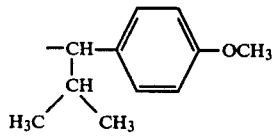 | | |
| 21 | 4-F | CN | 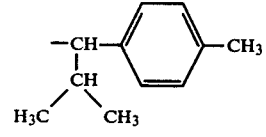 | | |
| 22 | 4-F | CN | 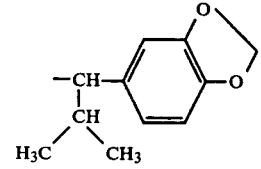 | | |
| 23 | 3-F | H | 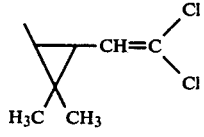 | | |
| 24 | 3-F | CN | 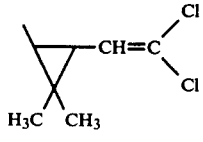 | | |

TABLE 1-continued

| Compound No. | R¹ | R² | R³ | Refractive index | Yield (% of theory) |
|---|---|---|---|---|---|
| 25 | 3-F | CN | 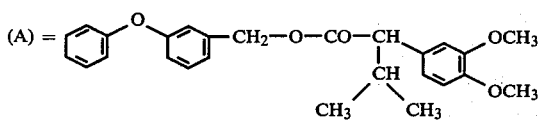 | | |

The insecticidal and acaricidal activity of the compounds of this invention is illustrated by the following examples wherein the compounds according to the present invention are each identified by the number (given in brackets) from the preparative examples and Table 1 hereinabove.

The known comparison compounds are identified as follows:

(A) = 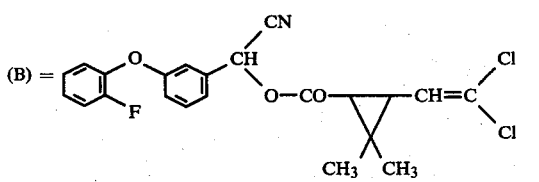

(B) = 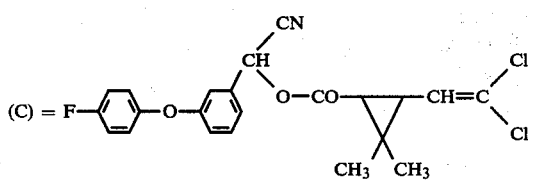

(C) = F—⟨⟩—O—⟨⟩—CH(CN)—O—CO—△(CH₃)(CH₃)—CH=C(Cl)(Cl)

EXAMPLE 4

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 2

(Insects which damage plants)
Phaedon larvae test

| Compounds | Active compound in % | Degree of Destruction 3 days |
|---|---|---|
| (A) | 0.1 | 100 |
| | 0.01 | 90 |
| | 0.001 | 0 |
| (B) | 0.1 | 100 |
| | 0.01 | 100 |
| | 0.001 | 100 |
| | 0.0001 | 0 |
| (7) | 0.1 | 100 |
| | 0.01 | 100 |
| | 0.001 | 100 |
| | 0.0001 | 100 |
| (6) | 0.1 | 100 |
| | 0.01 | 100 |
| | 0.001 | 100 |
| | 0.0001 | 100 |
| (8) | 0.1 | 100 |
| | 0.01 | 100 |
| | 0.001 | 100 |
| | 0.0001 | 90 |
| (2) | 0.1 | 100 |
| | 0.01 | 100 |
| | 0.001 | 100 |
| | 0.0001 | 100 |

EXAMPLE 5

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 3

| | (Mites which damage plants) Tetranychus test | |
|---|---|---|
| Active compounds | Active compound concentration in % | Degree of destruction in % after 2 days |
| (A) | 0.1 | 20 |
| (2) | 0.1 | 100 |
| (3) | 0.1 | 100 |
| (8) | 0.1 | 100 |

EXAMPLE 6

$LT_{100}$ test for Diptera
Test insects: Aedes aegypti
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 4

| | ($LT_{100}$ test for Diptera) Ades aegypti | |
|---|---|---|
| Active compounds | Active compound concentration of the solution in % | $LT_{100}$ |
| (C) | 0.0002 | 3 hrs = 0% |
| (2) | 0.0002 | 3 hrs = 100% |

EXAMPLE 7

Test with parasitic fly larvae
Emulsifier: 80 parts by weight of castor oil polyglycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*) were introduced into a test tube which contained about 3 ml of a 20% strength suspension of egg yolk powder in water, and which was fitted with cottonwool plugs of appropriate size. 0.5 ml of the active compound preparation was placed on this egg yolk powder suspension. After 24 hours, the degree of destruction in % was determined. 100% meant that all of the larvae had been killed and 0% meant that none of the larvae had been killed.

The active compounds, the concentrations of the active compounds and results can be seen from the table which follows.

Table 5

| | (Test with parasitic fly larvae) Lucilia cuprina (resistant) | |
|---|---|---|
| Active compound | Active compound concentration in ppm | Destructive action in % |
| (6) | 1,000 | 100 |
| | 300 | 100 |
| | 100 | 100 |
| (7) | 1,000 | 100 |
| | 300 | 100 |
| | 100 | 100 |

EXAMPLE 8

Tick test
Solvent: 35 parts by weight of ethylene glycol monomethyl ether
Emulsifier: 35 parts by weight of nonylphenol polyglycol ether To prepare a suitable formulation, three parts by weight of active compound were mixed with seven parts of the above-mentioned solvent/emulsifier mixture and the emulsion concentrate thus obtained was diluted with water to the particular concentration desired.

Adult, fully bloated ticks of the species *Boophilus microplus* (resistant) were dipped for one minute into these active compound preparations, 10 female specimens being used in each test. The specimens were then transferred into Petri dishes, the bottom of each of which was lined with a filter disc of corresponding size.

After 10 days, the activity of the active compound preparation was determined by examining the inhibition of the laying of eggs, as compared to untreated control ticks. The action was expressed as a percentage, with 100% denoting that eggs were no longer laid and 0% denoting that the ticks laid normal amounts of eggs.

The active compound examined, the concentration tested, the parasites tested and the findings obtained can be seen from the table which follows.

Table 6

| | Tick text/Boophilus microplus resist. | |
|---|---|---|
| Active compound | Active compound concentration in ppm | Destructive action in % |
| (7) | 10,000 | 100 |
| | 1,000 | 100 |
| (6) | 10,000 | 100 |
| | 1,000 | 100 |

It will be appreciated that the instant specification and examples are set forth by way of illustration and not limitation, and that various modifications and changes may be made without departing from the spirit and scope of the present invention.

What is claimed is:

1. A 3-phenoxy-fluoro-benzyl carboxylic acid ester of the formula

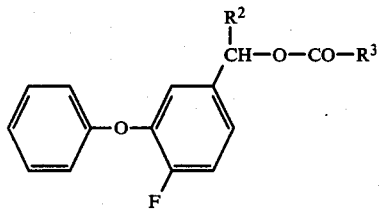

in which
R² is hydrogen, cyano or ethynyl,
R³ is

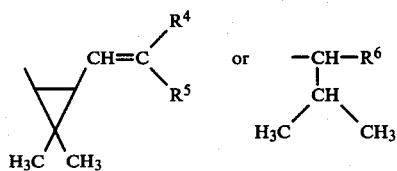

R⁴ and R⁵ represent chlorine, bromine or methyl, and
R⁶ is phenyl or phenyl substituted with halogen, alkyl with 1 to 4 carbon atoms, alkylthio with 1 to 4 carbon atoms, alkoxy with 1 to 4 carbon atoms, nitro or methylenedioxy.

2. An ester according to claim 1,
in which
R² is hydrogen or cyano, and
R³ is 2,2-dimethyl-3-(2,2-dichlorovinyl)-cyclopropyl, 2,2-dimethyl-3-(2,2-dibromovinyl)-cyclopropyl, 2,2-dimethyl-3-(2,2-dimethylvinyl)-cyclopropyl, α-isopropylbenzyl or α-isopropylbenzyl substituted with fluorine, chlorine, bromine, methylenedioxy, methoxy, ethoxy, methylthio, ethylthio, (straight-chain or branched) alkyl with 1 to 3 carbon atoms or nitro.

3. An ester according to claim 1, wherein such ester is 3'-phenoxy-4'-fluoro-benzyl 2,2-dimethyl-3-(2,2-dichlorovinyl)-cyclopropane-carboxylate of the formula

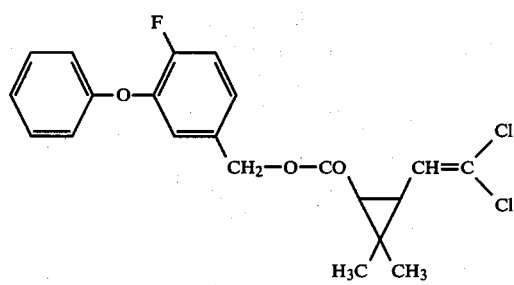

4. An ester according to claim 1, wherein such ester is 3'-phenoxy-4'-fluoro-α'-cyanobenzyl 2,2-dimethyl-3-(2,2-dimethyl-3-(2,2-dichlorovinyl)-cyclopropane-carboxylate of the formula

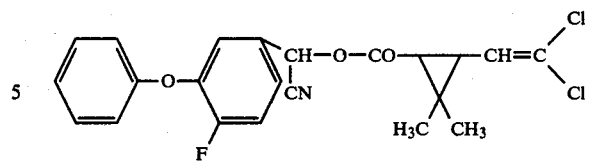

5. An ester according to claim 1, wherein such ester is 3'-phenoxy-4'-fluoro-α'-cyanobenzyl α-isopropyl-4-chlorophenylacetate of the formula

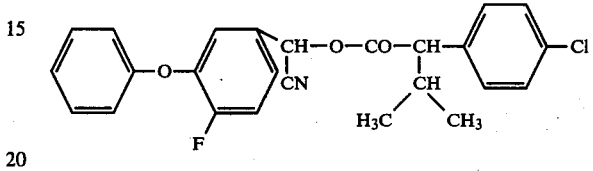

6. An ester according to claim 1, wherein such ester is 3'-phenoxy-4'-fluoro-α'-cyanobenzyl 2,2-dimethyl-3-(2,2-dibromovinyl)-cyclopropane-carboxylate of the formula

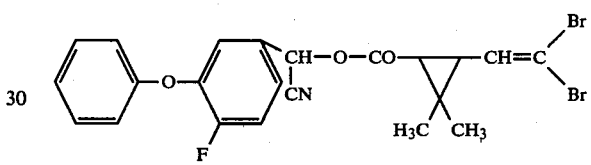

7. An ester according to claim 1, wherein such ester is 3'-phenoxy-4'-fluoro-benzyl 2,2-dimethyl-3-(2,2-dibromovinyl)cyclopropane-carboxylate of the formula

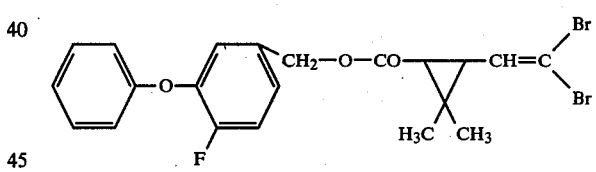

8. An arthropodicidal composition containing as active ingredient an arthropodicidally effective amount of an ester according to claim 1 in admixture with a diluent.

9. A method of combating arthropods which comprises applying to the arthropods, or to a habitat thereof, an arthropodicidally effective amount of an ester according to claim 1.

10. The method according to claim 9, wherein the ester is
3'-phenoxy-4'-fluoro-benzyl 2,2-dimethyl-3-(2,2-dichlorovinyl)-cyclopropane-carboxylate,
3'-phenoxy-4'-fluoro-α'-cyanobenzyl 2,2-dimethyl-3-(2,2-dichlorovinyl)-cyclopropane-carboxylate,
3'-phenoxy-4'-fluoro-α'-cyanobenzyl α-isopropyl-4-chlorophenylacetate,
3'-phenoxy-4'-fluoro-α'-cyanobenzyl 2,2-dimethyl-3-(2,2-dibromovinyl)-cyclopropane-carboxylate, or
3'-phenoxy-4'-fluoro-benzyl 2,2-dimethyl-3-(2,2-dibromovinyl)-cyclopropane-carboxylate.

* * * * *